(12) United States Patent
Termanini

(10) Patent No.: US 10,709,582 B2
(45) Date of Patent: Jul. 14, 2020

(54) SECUREMENT DEVICE FOR AN ORTHOPEDIC PROSTHESIS, THERMAL TREATMENT DEVICE FOR AN ORTHOPEDIC PROSTHESIS, AND METHODS OF USE

(71) Applicant: Joint Innovation Technology, LLC, Boca Raton, FL (US)

(72) Inventor: Zafer Termanini, Port Saint Lucie, FL (US)

(73) Assignee: Joint Innovation Technology LLC, Boca Raton, FL (US)

( * ) Notice: Subject to any disclaimer, the term of this patent is extended or adjusted under 35 U.S.C. 154(b) by 0 days.

(21) Appl. No.: 15/550,824

(22) PCT Filed: Aug. 11, 2017

(86) PCT No.: PCT/US2017/046502
§ 371 (c)(1),
(2) Date: Aug. 14, 2017

(87) PCT Pub. No.: WO2018/034983
PCT Pub. Date: Feb. 22, 2018

(65) Prior Publication Data
US 2018/0353307 A1    Dec. 13, 2018

(51) Int. Cl.
*A61F 2/46*      (2006.01)
*A61F 2/32*      (2006.01)
(Continued)

(52) U.S. Cl.
CPC .............. *A61F 2/4637* (2013.01); *A61F 2/32* (2013.01); *A61F 2/4603* (2013.01);
(Continued)

(58) Field of Classification Search
CPC ......... A61F 2/46; A61F 2/4607; A61F 2/4637
See application file for complete search history.

(56) References Cited

U.S. PATENT DOCUMENTS 4,126,924 A * 11/1978 Akins ................. A61F 2/30767
29/423
4,644,942 A    2/1987 Sump
(Continued)

FOREIGN PATENT DOCUMENTS

DE    7601139 U1    5/1976
DE    8400642 U1    5/1984
(Continued)

OTHER PUBLICATIONS

International Search Report for related application PCT/US2017/046502 dated Mar. 6, 2018.
(Continued)

*Primary Examiner* — Christopher J Beccia
(74) *Attorney, Agent, or Firm* — Norris McLaughlin, PA

(57) ABSTRACT

The present invention relates generally to devices and methods for firmly joining together components of a modular orthopedic prosthesis by securing female to male parts thereof together, and in particular a male part present in a modular component into a correspondingly configured female part (i.e., bore or recess) present in a further modular component thereof. Preferably the male part is tapered, and the bore or recess is correspondingly configured to provide a close tolerance fit therewith. In a preferred embodiment a securement device is used to join the components which securement device includes a heat resistant part or region which shields a heated part from its ambient environment; the securement device is useful in holding a component of an orthopedic prosthesis. In a further preferred embodiment the invention also comprises a heat treatment device which is issued to provide a suitable heat treatment to a component (or part thereof) of a modular orthopedic prosthesis. Methods of utilizing the securement device and the heat treatment
(Continued)

device during surgical implantation of modular orthopedic prosthesis is also disclosed.

14 Claims, 8 Drawing Sheets

(51) Int. Cl.
    *A61F 2/30*     (2006.01)
    *A61F 2/36*     (2006.01)

(52) U.S. Cl.
    CPC .. *A61F 2/4607* (2013.01); *A61F 2002/30332* (2013.01); *A61F 2002/30334* (2013.01); *A61F 2002/3654* (2013.01); *A61F 2002/465* (2013.01); *A61F 2002/4627* (2013.01); *A61F 2002/4628* (2013.01); *A61F 2002/4685* (2013.01)

(56) References Cited

U.S. PATENT DOCUMENTS

| | | |
|---|---|---|
| 4,676,798 A | 6/1987 | Noiles |
| 5,133,765 A | 7/1992 | Cuilleron |
| 5,264,680 A | 11/1993 | Seibold et al. |
| 7,708,739 B2 | 5/2010 | Kilburn et al. |
| 7,807,211 B2 | 10/2010 | Hossainy et al. |
| 7,879,042 B2 | 2/2011 | Long et al. |
| 8,152,855 B2 | 4/2012 | Tulkis et al. |
| 9,925,591 B2 | 3/2018 | Eonta et al. |
| 2003/0229357 A1 | 12/2003 | Dye |
| 2004/0117024 A1 | 6/2004 | Gerbec et al. |
| 2005/0233062 A1* | 10/2005 | Hossainy ............... A61F 2/82 427/2.1 |
| 2007/0162038 A1 | 7/2007 | Tuke |
| 2007/0173948 A1 | 7/2007 | Meridew et al. |
| 2014/0336776 A1 | 11/2014 | Taylor et al. |
| 2016/0052060 A1* | 2/2016 | Eonta ............... B22F 9/06 75/347 |
| 2017/0196701 A1 | 7/2017 | Behzadi et al. |
| 2018/0235764 A1 | 8/2018 | Moore et al. |

FOREIGN PATENT DOCUMENTS

| | | |
|---|---|---|
| FR | 2656792 A2 | 7/1991 |
| WO | 2014074647 A1 | 11/2013 |

OTHER PUBLICATIONS

Written Opinion of the International Search Authority for related application PCT/US2017/046502 dated Mar. 6, 2018.
Notice of References Cited in related U.S. Appl. No. 15/239,189, dated Nov. 20, 2018.

\* cited by examiner

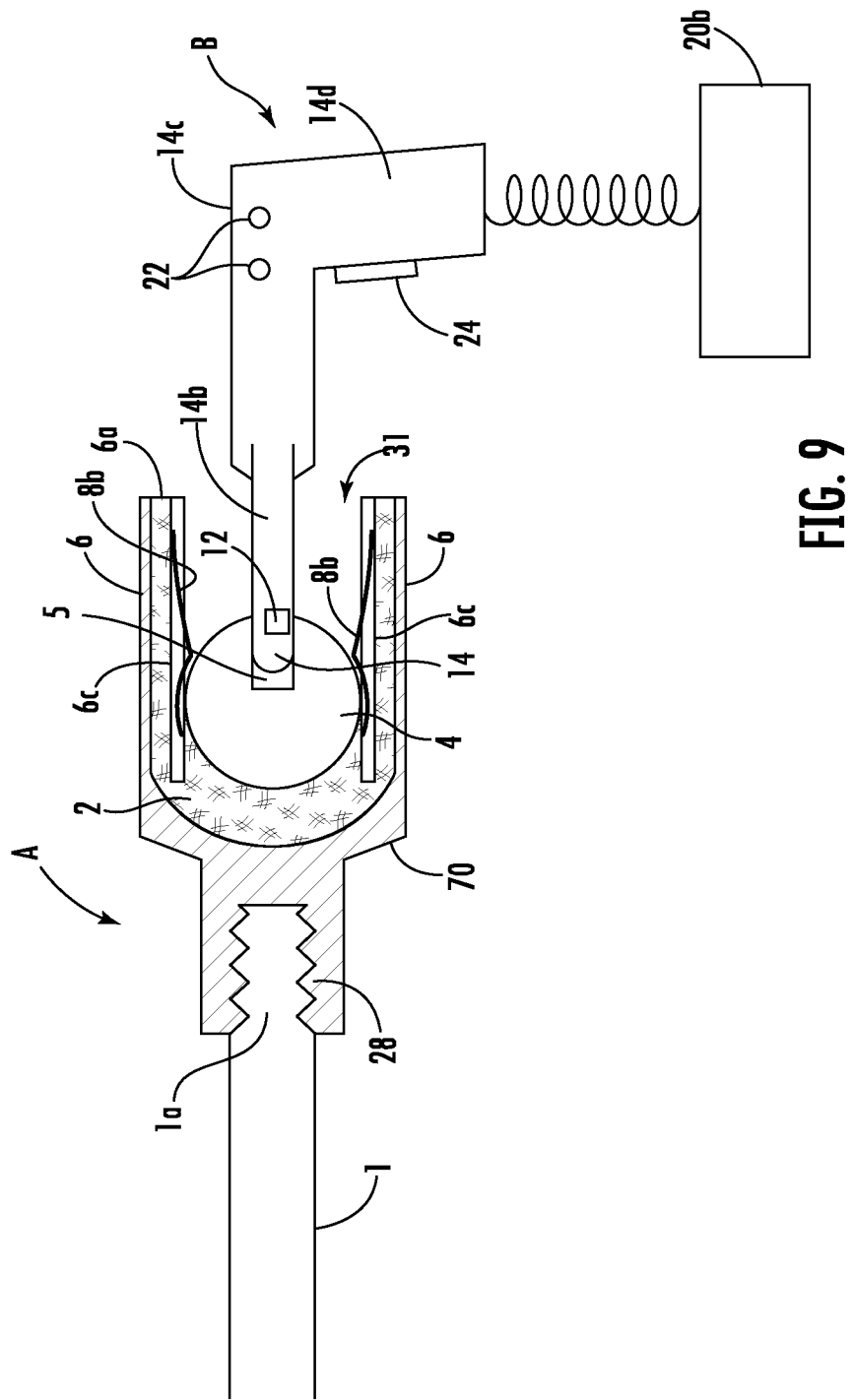

SECUREMENT DEVICE FOR AN ORTHOPEDIC PROSTHESIS, THERMAL TREATMENT DEVICE FOR AN ORTHOPEDIC PROSTHESIS, AND METHODS OF USE

This is a patent application filed as a 35 USC 371 of PCT/US2017/46502 filed 11 Aug. 2017, which in turn claims the priority benefit of U.S. Ser. No. 15/239,189 filed 17 Aug. 2016. The entire contents of these foregoing applications is herein fully incorporated by reference thereto.

The present invention relates generally to devices and methods for firmly joining together components of a modular orthopedic prosthesis by securing female to male parts thereof together, and in particular a male part present in a modular component into a correspondingly configured female part (i.e., bore or recess) present in a further modular component thereof. Preferably the male part is tapered, and the female part is a bore or recess which is s correspondingly configured to provide a close tolerance fit with the male part. In a preferred embodiment a securement device is used to join the components which securement device includes a heat resistant part or region which shields a heated part or component from its ambient environment; the securement device is useful in holding a component of an orthopedic prosthesis. In a further preferred embodiment the invention also comprises a heat treatment device which is issued to provide a suitable heat treatment to a component (or part thereof) of a modular orthopedic prosthesis. Methods of utilizing the securement device and the heat treatment device during surgical implantation of modular orthopedic prosthesis is also disclosed.

The present invention thus relates to apparatus and methods which are used in the assembly of an orthopedic prosthesis from a plurality of components; in particular the apparatus and methods are particularly well adapted for use in conjunction with a prosthesis implanted in a human body to at least partially replace a shoulder, elbow, hip or knee joint via a surgical procedure. Such orthopedic prosthesis are typically assembled from two or components parts, e.g., an implantable stem which is affixed to a bone and an implantable correspondingly sized cup which is also implanted or affixed to a bone. These two components themselves, or in conjunction with further components, may operate as a replacement joint for the treated patient.

Examples of such orthopedic prosthesis which incorporate a tapered part are widely known and include, inter alia, U.S. Pat. No. 8,313,531 B2 for "Interlocking Reverse Hip Prosthesis"; US 2014/0156011 A1 for "Modified Reverse Joint and Revision Prosthesis"; US 2014/0200675 A1 for "Lined Femoral Cup". These depict multi-part implantable orthopedic prosthesis which comprise a tapered part, viz. a Morse taper. As is readily seen from these certain of the components and parts of the implantable orthopedic prosthesis are typically constructed of durable materials, namely metals and/or metal alloys (hereinafter collectively referred to as "metals") which are biocompatible and expected to have a long service life. Such components of an implantable orthopedic prosthesis are typically formed or machined to very exacting dimensions and tolerances. In some embodiments surface regions or part of a component formed of metals/metal alloys may also have specific surface treatments which may aid in one or more ways, such as in reducing corrosion or improving the growth of bone onto the surfaces of such parts.

Modular orthopedic prosthetics frequently include components having "male" parts (or elements) which are dimensioned to be inserted within a correspondingly dimensioned cavity or bore part ("female" parts or elements) of a further component. Within the operating room, a surgeon is typically provided with a plurality of discrete components (which may be in the form of a "kit") wherein the surgeon, during a surgical procedure, may select amongst available discrete components. The components may for example vary in their individual dimensions or configurations depending upon their function, and from these the surgeon may assemble a suitably configured orthopedic implant which will be implanted in the patient's body. However, such 'modularity' it the provision of multiple components for assembly by the surgeon is frequently incriminated in the subsequent release of metal wear debris within the patient's body which take place over a time period of weeks, months or years subsequent to the implantation of the orthopedic implant from assembled modular components. Such metal wear debris may be responsible for local inflammatory reactions ultimately leading to osteolysis. Resultant pain and functional disability has frequently required subsequent and sometimes extensive surgical revisions of the previously implanted orthopedic prothesis formed from assembled modular components and/or significant clinical and functional limitations imposed upon the patient.

It is also known to the art that in both in-vivo as well as well as in-vitro conditions that that micromotion between a tapered male part and a correspondingly dimensioned female part is a major culprit due to "fretting corrosion", notwithstanding that both parts are typically machined metal parts fabricating with very exacting tolerances. Fretting corrosion typically occurs at metal surfaces, and the damage to the components of implanted orthopedic prosthetics is usually induced under load and in the presence of repeated motion, and/or by vibration. Such fretting corrosion occurring at or near the interfacial contact surfaces of a male part seated or attached within a correspondingly dimensioned female part is particularly desirably to be avoided. Such fretting corrosion may damage a protective oxide layer which may otherwise form or be present at the interfacial contact surfaces between the parts and such damage may initiate a corrosive cascade effect, wherein in the presence of impurities and local tissue fluid in the region of the implanted modular orthopedic prosthesis triggers galvanic corrosion by reduction of the pH at or near the interfacial contact surfaces of the male part seated or attached within the correspondingly dimensioned female part, which induces release of metal-hydride ions thereby causing further damage to the interfacial contact surfaces.

Whereas during assembly of components of an implantable modular orthopedic prosthesis manual impacting using a hammer is known to be used, such is not always satisfactory. It has been reported that manual impaction of the components is frequently insufficient in reducing or eliminating micromotion between the components since cyclic loading of normal gait and other daily activities of a patient causes the components to cantilever and move. Further while the use of additional corresponding machined features such as mating screw threads, splines, or other non-smooth machined features in one or both of the interfacial contact surfaces of the tapered male part seated and a correspondingly dimensioned female part might be considered as a remedy, such require additional machining, and inherently impart an increase in surface area which in turn increases the likelihood and degree of galvanic corrosion initiated by reduction of the pH at or near their interfacial contact surfaces. Such shortcomings, and the increased complexity in both fabricating as well as in properly assembling an orthopedic prosthesis from modular components having such additional corresponding machined features dissuades the use of such modular components having non-smooth surfaces at the interfacial surface regions or interfacial contact surfaces of their male part(s) and the correspondingly dimensioned female part(s) thereof.

The present invention addresses and overcomes the foregoing shortcomings in the prior art.

In one aspect, the present invention provides an improved orthopedic prosthesis assembled from modular components which orthopedic prosthesis are expected to exhibit no or substantially diminished fretting corrosion due to the effects of micromotion induced within the implanted orthopedic prosthesis.

In another aspect the present invention provides an improved orthopedic prosthesis assembled from modular components which orthopedic prosthesis are expected to exhibit no or only substantially diminished micromotion between assembled male and female parts thereof.

In another aspect the present invention provides a method of assembling such an improved orthopedic prosthesis from discrete modular components, at least one component having a male part, and at least one component having a correspondingly dimensioned female component adapted to receive and retain the male part, wherein the assembled prosthesis exhibits no or diminished fretting corrosion due to the effects of micromotion induced within the implanted. orthopedic prosthesis.

In another aspect the present invention provides a method of assembling such an improved orthopedic prosthesis from discrete modular components, at least one component having a male part, and at least one component having a correspondingly dimensioned female component adapted to receive and retain the male part, wherein the assembled prosthesis exhibits no or diminished micromotion between the assembled male and female parts.

In a still further aspect there is provided an apparatus and method for the use of the apparatus in assembling such an improved orthopedic prosthesis as described herein.

A yet further aspect of the invention is a surgical method which includes the step of firmly joining components forming a modular orthopedic prosthesis in-vivo, within a human patient.

These and further aspects of the invention will become more apparent from a consideration of the following specification and accompanying drawings.

An inherent property of metals (and/or metal alloys) is a tendency to change shape and volume in response to a change in temperature through heat transfer. Expansion and contraction of components by heat was widely used to fit metallic parts over one another, such as hot riveting of structural steel components in buildings. In other mechanical applications, the diameter of an undersized bore of a metallic bushing can be increased through heating to increase the diameter, which then may allow for it to be fitted about a circular shaft, and subsequent cooling may achieve a "shrink fit". Such "shrink fitting" of mechanical components in machinery is known; typically metal components require a period of sufficient heating in order to cause sufficient expansion of the metal component to subsequently permit for forming an assemblage, viz, the insertion or removal of the heated metal component with another element or component.

The inventor has found that the substantial or complete elimination of micromotion between smooth surfaced male parts of a component of a modular implantable orthopedic prosthesis and a correspondingly dimensioned female part of a component of the modular implantable orthopedic prosthesis can be attained, and that such significantly reduces the corrosion of the contact surfaces of these contacting parts. Such is achievable by the use of an apparatus, and a corresponding method for its use. Such a result may occur by first thermally treating one or more components or parts of a modular implantable orthopedic prosthesis prior to assembly with one or more further components or part thereof of the modular implantable orthopedic prosthesis. Such assembly occurs however when the thermally treated parts or components are a temperature which is elevated with regard to further non-thermally treated components during assembly such that contraction of the thermally treated parts or components occurs. Such thermal pretreatment provides for a significant reduction in the in-vitro, and in particular the in-vivo, fretting corrosion between interfacial contact surfaces of elements of an assembled modular implantable orthopedic prosthesis by substantially or completely eliminating "micromotion" between two or more assembled male and female parts of components of the prosthesis. During the assembly of the implantable orthopedic prosthesis from two or more components, e.g., modular components, the thermal pretreatment of at least one of the components and/or parts thereof and its resulting thermal expansion permits for the subsequent formation of a mechanically secure "shrink fit" type juncture between the parts and/or components and a non-thermally pretreated part or component when the thermally pretreated component and/or part thereof is cooled from its prior elevated temperature imparted to it by the thermal pretreatment step to an ambient temperature. Such an ambient temperature may be between about 50° F.-100° F. (about 10° C.-38° C.) with the latter being slightly in excess of "normal" human body temperature. Such a thermal contraction in the previously thermally pretreated component or part thereof provides for a shrinking of the component or part and due thereto, permits for a mechanically secure "shrink fit" type juncture therebetween as such provides considerable contact pressure at the interfacial contact surfaces therebetween which typically exceed contact pressures which are typically generated at interfacial contact surfaces resulting only from by manual impaction, e.g, tapping or hammering together mating modular components or parts thereof, of an implantable orthopedic prosthesis.

Such a result is particularly evident wherein the junction between mating parts of modular components of an implantable orthopedic prosthesis is formed between a tapered male part and a correspondingly dimensioned female part, namely a bore or a cavity which accepts the tapered male component.

Such a result is also particularly evident wherein the junction between mating parts of modular components of an implantable orthopedic prosthesis is formed between a non-tapered male part and a correspondingly dimensioned female part, namely a bore or a cavity which accepts the non-tapered male component.

In preferred embodiments, the tapered male part may be a frustoconical element, or a tapered shank. The configuration of the taper may be any which is complementary to the dimensions of the correspondingly dimensioned female part, which is preferably a bore or cavity which accepts the tapered male component and with which it form a "shrink fit" junction. The angle of the taper relative to a central axis of the shank or male part may vary, but advantageously has an angle of between about 0.5 and 5 degrees of arc, preferably between about 1 and 3 degrees. Conventional configurations of such tapers are preferred, include one or more of: a Morse taper, a Jacobs taper, a Brown & Sharpe taper, a Jarno taper, with a Morse taper, especially Morse tapers having an angle of between about 1 and 5 degrees of arc being particularly preferred. The exterior sidewall surface of the taper or male part may be a smooth surface, but may optionally include a coating or a roughened surface which may facilitate interfacial contact with the bore or cavity which accepts the tapered male component. Preferably the exterior sidewall surface of the taper excludes splines or screw thread elements which are machined thereinto.

In a preferred method of the invention, prior to assembly onto the male part, the female component or a part thereof is first subjected to a thermal treatment step wherein the sufficient energy, preferably thermal energy, is supplied to the female component or part such that at least one dimension, preferably the width dimension of a bore or cavity which is dimensioned to accept the male part is at least slightly enlarged as compared to the same bore or cavity at room temperature, viz. 68° F. (20° C.). The relative amount or percentage increase in the at least one dimension, (e.g. preferably the width, or other sized part of the female component adapted to receive the male part,) need not be particularly large and may be as little as a 0.00001% to as much as a 5% relative increase (or more) in the dimension. It is only required that the at least one dimension of the female part, i.e., bore or cavity, be increased due to the thermal treatment step, e.g. by a heating step, to reversibly expand this dimension such that subsequent to the thermal treatment step and when the female component is returned to room temperature that it returns substantially (viz. to within 99.99%-100%) of its original dimension. By way of non-limiting example, the at least one dimension of the female component may be the diameter of a part of the bore or cavity at one or more parts thereof, such as at the entry or margin thereof through which the male part is inserted, or may be the diameter or a cross-dimensional length at a point perpendicular to the a part of the bore or cavity somewhere between its ends, or between its open ends, or between its one open end and a closed end, whichever is appropriate. The thermal treatment may be supplied by any means, but is preferably supplied by a thermal treatment device as described hereinafter. Once coupled with a non-thermally treated component or part thereof, the thermally treated component or part thereof may be cooled and returned to a reduced temperature by irrigating or dousing it with a liquid, as a sterile saline composition or with sterile water. Ideally the thermally treated parts or components are retained at an elevated temperatures relative to the non-thermally treated parts or components used to form components during their assembly, so that upon subsequent cooling of the thermally treated parts or components, thermal "shrink-fitting" occurs. In preferred embodiments the thermally treated parts or components are at least about 10° C., and more preferably (in order of increasing preference) are at least 20° C., 30° C., 40° C., 50° C., 60° C., 70° C., 80° C., 90° C., 100° C., 120° C., 140° C., 160° C., 180° C., 200° C., 220° C., 240° C. warmer than the non-thermally treated parts or components to which they are joined. In a preferred embodiment thermally treated parts or components are heated to a temperature in the range of about 220° C.-275° C., more preferably about 240° C.-260° C., and especially preferably to about 250° C., It is also to be clearly understood that the bore or cavity need not have a geometry which is symmetrical about a center axis as would occur if the bore or cavity were of a circular, cylindrical or frustoconical cross-section. It is to be recognized that female components may include bores or cavities of non-symmetrical geometries as well, and thus with these may be used male components and parts thereof may also have non-symmetrical geometries as well. Such include elliptical, oval and other cavities. Bores may be straight walled, that is to say the cross-sectional geometry remains constant from an open end of the bore, to a further terminal end, or further distal opening thereof. But bores may also have non-symmetrical geometries, namely that the cross-sectional geometry may vary from an open end of the bore, or from the open end of the cavity to a further terminal and, further distal opening thereof. Such bores and cavities may have distal ends which are flat, or maybe non-flat but this is not necessarily the case. Indeed, other irregular geometries may also be extant.

As noted the amount of thermal energy to be supplied in the thermal treatment step to a component or part thereof need be sufficient in order to cause sufficient thermal expansion of a modular component or part thereof to so cause a reversible thermal expansion of the said component or part thereof, and to thereby cause a compressive shrink-fit type juncture between a male part of a component and a female part of a component. The amount of energy which is necessary to achieve this will depend on a several factors including but not limited to: the nature of the metal, the thermal expansion coefficient of the metal of the part or component being treated, the mass of the component or part thereof to be treated, the dimensions and geometric configuration of the component and/or part thereof, and the presence of any surface coatings or surface treatments upon the component or part subjected to the thermal treatment step. As would be readily understood, these factors play a role upon the determination of the amount of energy required to be introduced into the modular component or part thereof to be treated to bring about a satisfactory degree of thermal expansion so to allow for it to be placed, preferably concurrently also with the application of a physical force such as physical compression or impaction, upon a corresponding component or part thereof, will vary specifically with the component and/or part being treated, but such may be determined by routine experimental or empirical techniques methods. For example a component or part thereof may be heated and the time and energy of heating noted, which time and energy which is satisfactory to bring about a satisfactory amount of thermal expansion noted. Thereafter, similar or like component or parts may be subjected to the same thermal treatment regimen so to bring about a similar satisfactory degree of thermal expansion. When the component or parts are subjected to a desired or satisfactory amount of thermal expansion, the component or part may be coupled or joined to a corresponding component or part which has not been subjected to a thermal treatment step, such that the cooling thermally treated component or part forms a shrink type fit. Again, thermal treatment may be supplied by any means such as by exposing the thermally treated component or part to a suitable energy source. Non-limiting examples include: electrical induction heating, immersion in a heated liquid bath, such as boiling water or other sterile solution, heating in an oven to a sufficient temperature, heating under increased pressure such as an autoclave, immersion in a bed of a heated granular or particulate material, or via other means or via the use of other devices not expressly recited here. Advantageously however, heat treatment is supplied by a thermal treatment device as described hereinafter. Again, subsequent to joining with a further component or part thereof, cooling may be facilitated by providing cold sterile irrigation fluid to the joined components and/or parts thereof which is readily available in operating rooms.

The apparatus and method of the invention are particularly adapted for the assembly devices and methods for firmly joining together two or more components together of a modular orthopedic prosthesis by securing male and female components thereof and especially wherein the modular orthopedic prosthesis are used in the replacement of shoulders, elbows, knees and in particular hips in human patients. Non-limiting examples of such prosthesis include:

1) Surgically implantable hip prosthesis wherein the femoral implant includes a stem or shaft having a part which is embedded within a femur, and which has extending therefrom a ball (or similarly configured three-dimensional geometric surface). The hip prosthesis also includes a complementary acetabular cup implantable in a pelvis which comprises a cavity or a socket which contacts a part of the ball (or other three-dimensional geometric body, which may include a concavity corresponding to a part of the ball) which extends from the stem or shaft of the femoral implant. An interfacial surface is defined between the ball and the acetabular cup when such are in contact with each other. The femoral ball may be affixed via a male part into a female part (bore and/or cavity) using the apparatus and method of the invention. In such implantable hip prosthesis it is common that an implantable femoral stem is provided which includes a female part, and a femoral ball having an extending male part which is first treated using the apparatus of the invention, and which may affixed to the femoral stem which may have been implanted in the patient's femur. Non-limiting examples of such are known to the art, e.g.: U.S. Pat. Nos. 5,462,563, 8,323,346, and 9,005,306.

2) Improved types of implantable hip prostheses which are sometimes referred to as "reverse cup" types. In such types, the femoral implant includes a stem or shaft having a part which is embedded within a femur, and which has extending therefrom a femoral cup, which comprises a cavity or a socket. The hip prosthesis also includes a complementary acetabular cup implantable in a pelvis which acetabular cup includes a ball (or similarly configured three-dimensional geometric surface) at least partially present therein. The interfacial surface is defined between the cavity or socket of the femoral cup, and the ball of the acetabular cup when in contact with each other. Non-limiting examples are also known to the art, e.g.: U.S. Pat. Nos. 8,313,531, 8,845,743, 8,992,627, and 9,119,724.

In a still further aspect there is provided an apparatus and method for the use of the apparatus in assembling such an improved orthopedic prosthesis as described herein.

According to one method of the invention the thermal expansion of the modular component or part thereof occurs within or near the locus of a human patient. To facilitate this, there is provided a securement device which includes a heater element and a heat resistant part or region which shields the heater element from human tissues within or near the locus of a human patient. Further, the securement device is useful in holding and concurrently providing heat to a part or a modular component of an orthopedic prosthesis, and may assist with the placement of the heated part or a modular component within a human patient. An exemplary securement device is disclosed and described with reference to the drawings, in which:

FIG. 9 is a partial cross-sectional view of both a further embodiment of a securement device, and a hand-holdable thermal treatment device, illustrating the direct heating of a tapered cavity within a modular component, viz., a ball.

Various other objects, features and attendant advantages of the present invention will become fully appreciated as the same becomes better understood when considered in conjunction with the accompanying drawings, in which like references characters designate the same or similar parts throughout the several views, and wherein:

Turning now descriptively to the drawings, in which similar references characters denote similar elements throughout the several views, the attached figures illustrate certain preferred embodiments of the invention.

Figure 1:
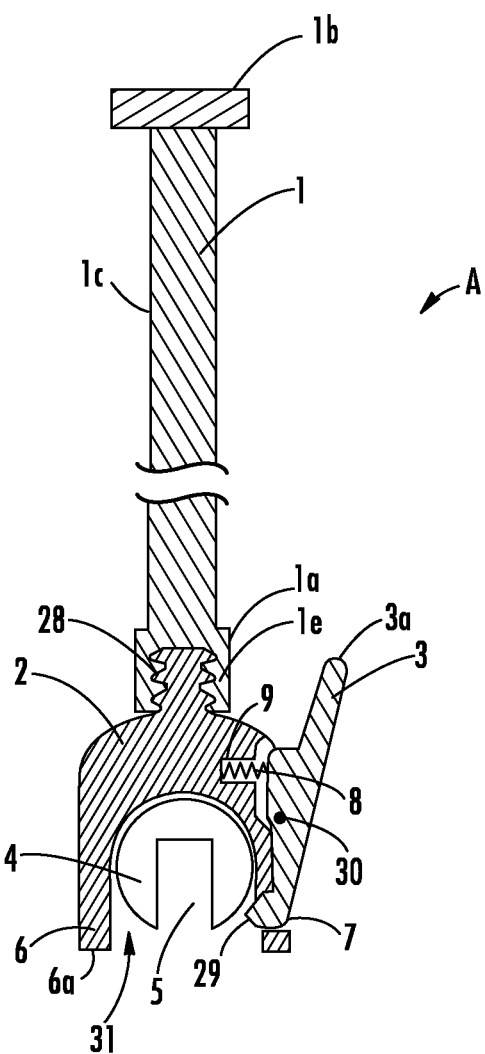
FIG. 1 depicts a cross-sectional view of a securement device, which may be used to both hold, or removably retain a modular component within, and to facilitate impaction of the retained modular component.
Figure 2:
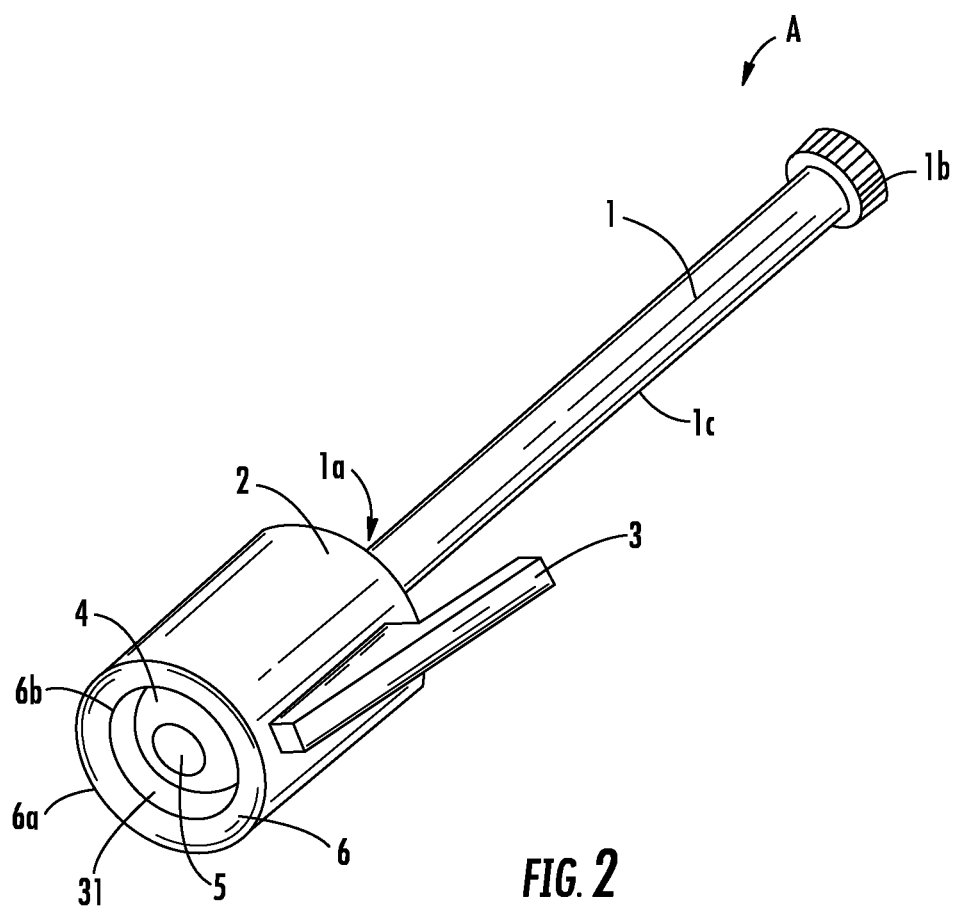
FIG. 2 is a perspective view of the securement device of FIG. 1.

In FIGS. 1 and 2 is depicted a preferred securement device A, comprising an impactor handle 1 which is attached at a distal part 1a thereof to a cylindrically shaped heat resistant impactor body 2. The impactor handle has a proximal end 1b, and an intermediate shaft 1c which extends to the distal end 1a which includes a threaded end 1e via which the handle 1 is secured to the impactor body 2 via a set of mating threads 28. While not depicted in the figure, the impactor handle 1 may be affixed to the impactor body 2 by any other suitable configuration or means, i.e., a friction fitted distal part 1a fittable into a suitably sized socket in the place of the threated end 1e, or other configuration may also be used. The impactor body 2 extends further distally from the threaded end 1e to form a protective circular thermal skirt 6 which extends and terminates at a base 6a. The impactor body 2 between the base 6a and the threads 28 defines a cavity 31 within which is configured to and removably retain a modular component or part thereof which has been subjected to thermal treatment as previously described. In the depicted embodiment, the cavity 31 is generally hemispherical in shape as the particular embodiment is designed to accommodate an articular metal ball 4 as the modular component. Similarly to accommodate such an articular metal ball 4, the base 6a is substantially circular in configuration. As is also visible from both FIGS. 1 and 2, the articular metal ball 4 comprises as a female part, a tapered cavity 5, configured to receive as a corresponding male part, i.e., a Morse taper (not shown.)

The impactor body 2 and the extended skirt 6 thereof are fabricated from a heat resistant material that is effective in withstanding temperatures of at least, but preferably in excess of 275° C. without deformation or melting. Non-limiting examples of such materials may include resins, composites, ceramics, polymers, fiberglass or combination thereof. Preferred are impact resistant materials which may be reinforced with dissimilar materials (i.e., fibers, roving, wire, particulates) which permit for the application of a striking force to the proximal end 1b of the impactor handle 1, such as may be supplied by a hammer or other manually operable striking instrument, or as may be supplied by a powered (i.e., electrical, hydraulic and/or pneumatic) source (i.e, an electrically driven impact hammer or similar tool.) To keep the ball 4 secured inside the impactor cavity 31 after heating, in the depicted embodiment there is also provided a lever 3 having a claw end 29. The lever 3 is situated on a part of the skirt 6 and the claw end 29 extends through an opening 7 extending through the skirt 6, such that it contacts a part of the ball 4. The lever 3 is pivotable about a pin 30; intermediate the pin 30 and the proximal end 3a of the lever 3 is a spring 8 located within a cylindrical cavity 9. The spring 8 is an expansion spring biased to extend outwardly against a part of the lever 3, thereby urging the claw end 29 inwardly and against the ball 4.

Figure 3:
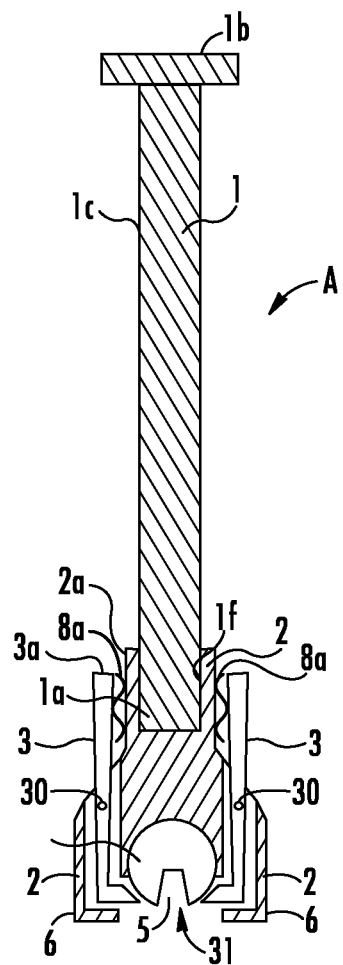
FIG. 3 depicts a cross-sectional view of a further embodiment of a securement device.

Although not illustrated in FIGS. 1 and 2, a skilled artisan would readily understand that one or more further similar levers 3 and corresponding openings 7, pins 30, springs 8 in cavities 9 may be advantageously provided to provide additional levers which may provide additional support and retention of the ball 4. Such an embodiment is illustrated in FIG. 3 which depicts in a cross-sectional view a further securement device A having an impactor handle 1 which is attached at a distal part 1a thereof to a cylindrically shaped heat resistant impactor body 2, wherein the distal part 1a is tapered, and forms an interference fit with a corresponding tapered cavity 2a present in the impactor body 2. Such allows for the separation of the impactor handle 1 from the impactor body 2 without requiring any rotation therebetween. In the figure, there are depicted leaf springs 8a which function similarly to the spring 8 of FIG. 1, but differ in that leaf springs 8a are biased against an exterior sidewall 2a of the impactor body 2. When two such levers 3 are positioned diametrically opposed as shown, such facilitates the release of the ball 4 by squeezing the two ends 3a of the levers 3 together, e.g., against the springs 8a. The provision of multiple levers 3 may provide improved retention of the ball 4 (or other component) within the cavity 31.

Figure 4:
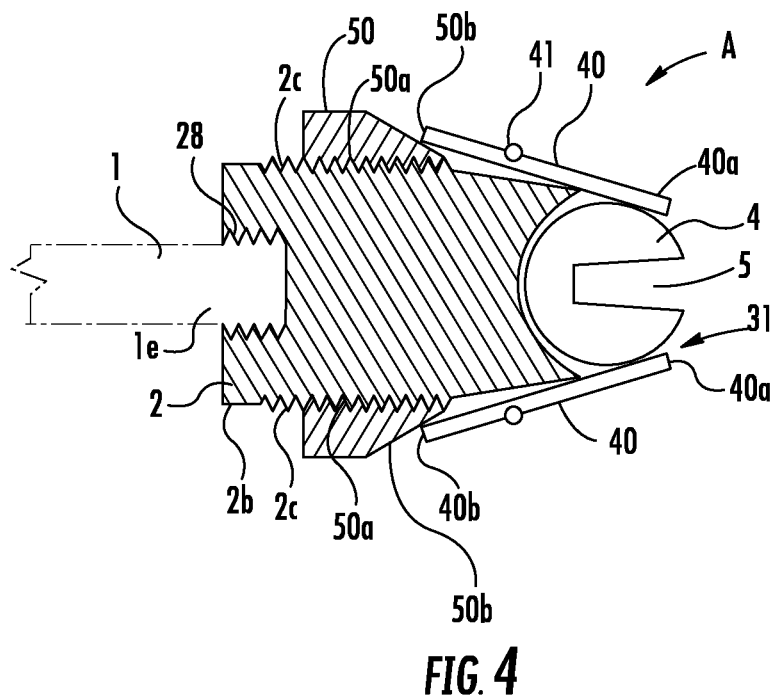
FIG. 4 depicts a cross-sectional view of a another embodiment of a securement device.

Also while not illustrated in FIGS. 1 and 2, a skilled artisan would readily understand that the lever 3 may be omitted and in its stead a collet may be provided wherein elements of the collet would be extended and grip one or more parts of the ball 4 when the collet is in a first position, while in a second position the elements of the collet would be retracted to release the ball 4. Such an embodiment is shown in the cross-sectional view of FIG. 4 depicting a further securement device A. As is seen the distal end 1a of the handle (only part of which is shown) is coupled to a part of a cylindrically shaped heat resistant impactor body 2 via a set of intermediate mating threads 28. Here an extended skirt 6 is omitted, which is in part replaced by pivot plates 40 each having a lower end 40a and an upper end 40b, which are pivotable about an annular ring 41 which retains the pivot plates 40 in position relative to the impactor body 2. A collet ring 50 spans the circumference of the impactor body 2 and has inner mating threads 50a which correspondingly engage surface threads 2c present on the impactor body 2, such that when the collet ring 50 is rotated, it causes the ramped part 50c of the collet ring 50 to move towards or away from the upper ends 40b, which correspondingly pivots the lower ends 40a towards or away from the ball 4 present in the cavity 31. Selective placement of the collet ring 50 by such rotation allows for a controllable degree of gripping pressure on parts of the ball 4, which may be desirable in certain circumstances. It is to be understood that the use of such an assemblage shown in FIG. 4 may be adapted for other thermally treated components other than a ball 4 which is depicted for sake of convenient illustration.

Figure 5:
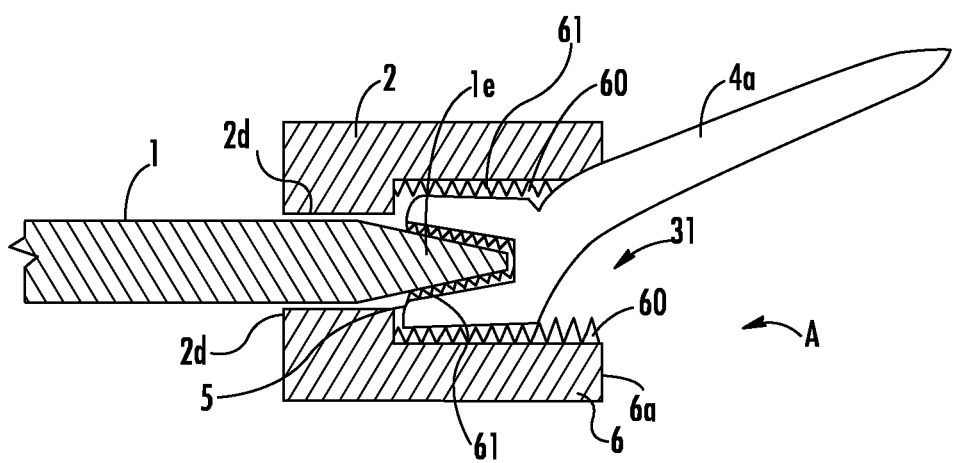
FIG. 5 illustrates a cross-sectional view of a further embodiment of a securement device.

Also while not while not illustrated in FIGS. 1 and 2, a skilled artisan would readily understand that the lever 3 may be omitted and in its stead a part of the cavity 31 could be lined with a resilient compressible material which is configured and/or dimensioned to removably retain the ball 4 (or other thermally treated component) within the cavity 31, but that after coupling of the ball 4 to a further non-thermally treated component, the impactor body 2 could be withdrawn causing the sufficient deformation of the resilient compressible material so that the ball 4 (or other thermally treated component) would be released from within the cavity 31. As a non-limiting example a ring or torus of such a resilient compressible material could be fitted within the cavity 31 near the or coincident with the base 6a. An embodiment of such securement device A is shown in the cross-sectional view of FIG. 5. In the embodiment the handle 1 (only part of which is shown) is encircled by an impactor body bore 2d passing therethrough which allows for the impactor body 2 to be slidably displaced along the shaft 1c; such facilitates the engagement of the tapered (or otherwise shaped) distal end 1a into the tapered cavity 5, which is configured to receive as a corresponding male part, (i.e., a Morse taper,) of a thermally treated component, here illustrated as a stem 4a such as may be used for implantation into a bone, e.g. femur, tibia or other bone of a human body. The cavity 31 of the impactor body 2 includes an interior lining 60 of a deformable resilient material which may be at least partially compressible and/or be resiliently deformable, and in such a condition may facilitate the retention of the thermally treated component within the impactor body 2. While to be understood to be optional (but is included in preferred embodiments) within the depicted embodiment, the distal end 1a includes at a surface thereof a surface lining 61 of a deformable resilient material which may be at least partially compressible and/or be resiliently deformable and in such a condition may facilitate the retention of the thermally treated component in the cavity 5 thereof. The interior lining 60 and the surface lining 61 may be of the same or of different deformable resilient materials. In the embodiment of FIG. 5, the non-spherical shape of the stem 4a is reliably retained by the securement device A by at least the interior lining 60 of a deformable resilient material, and the handle 1 engaged in the cavity 5 (female part). The impactor body bore 2d allows for the selective placement of the impactor body 2 and the skirt 6 during a surgical procedure, namely during the initial insertion of the stem 4a, it may be advantageous to keep the skirt 6 in a position to shield the thermally treated part of the stem 4a from nearby tissues in the patient's body, yet the skirt 6 may be lifted away to allow for an unobstructed view of the stem 4a if desired or necessary, and once viewed the skirt 6a may be returned to its prior position.

In yet another configuration not shown in FIGS. 1 and 2 but readily understood to a skilled artisan from the following description, the dimension of the opening 6b (FIG. 2) of the cavity 31 is slightly smaller than the largest or widest dimension of the ball 4 (or other thermally treated component) such that it is retained within the cavity. The impactor body 2 however has at least one moveable part which extends through the skirt 6 such that the impactor body 2 can be configured to increase the dimension of the opening 6b to allow for the ball 4 (or other thermally treated component)

to be released from within the cavity. For example the impactor body 2 may be formed of two or more component parts which when assembled retain the ball 4 (or other thermally treated component) but when partially disassembled allow for the release of the ball 4 (or other thermally treated component) through the opening 31 after the ball 4 (or other thermally treated component) has been joined to a non-thermally treated component or part thereof. In a simple embodiment, the impactor body is formed of two halves, which can be moved between 'open' and 'closed' positions, such as is shown in the partial-phantom, partial cross-sectional view of FIG. 6. As is seen thereon the impactor body 2 is formed of two halves 2',2" which when in closed position as shown, grasp a thermally treated component by at least the thermally treated part thereof, herein a part of a stem 4a which is gripped by complementary least partially compressible and/or be resiliently deformable and in such a condition may facilitate the retention of the thermally treated component in complementary cavity parts 31',31" which together define the cavity 31 when the impactor body 2 is a closed position. The complementary cavity parts 31',31" formed of the compressible material 60 operate to grip at least the thermally treated part of the stem 4a.

In such a position the impactor body 2 may be used to place the component, here the stem 4a within a human body, and thereafter the two halves 2',2" may be hinged open such as about a pin 30 to release the stem 4a from within the impactor body 2.

Figure 6:
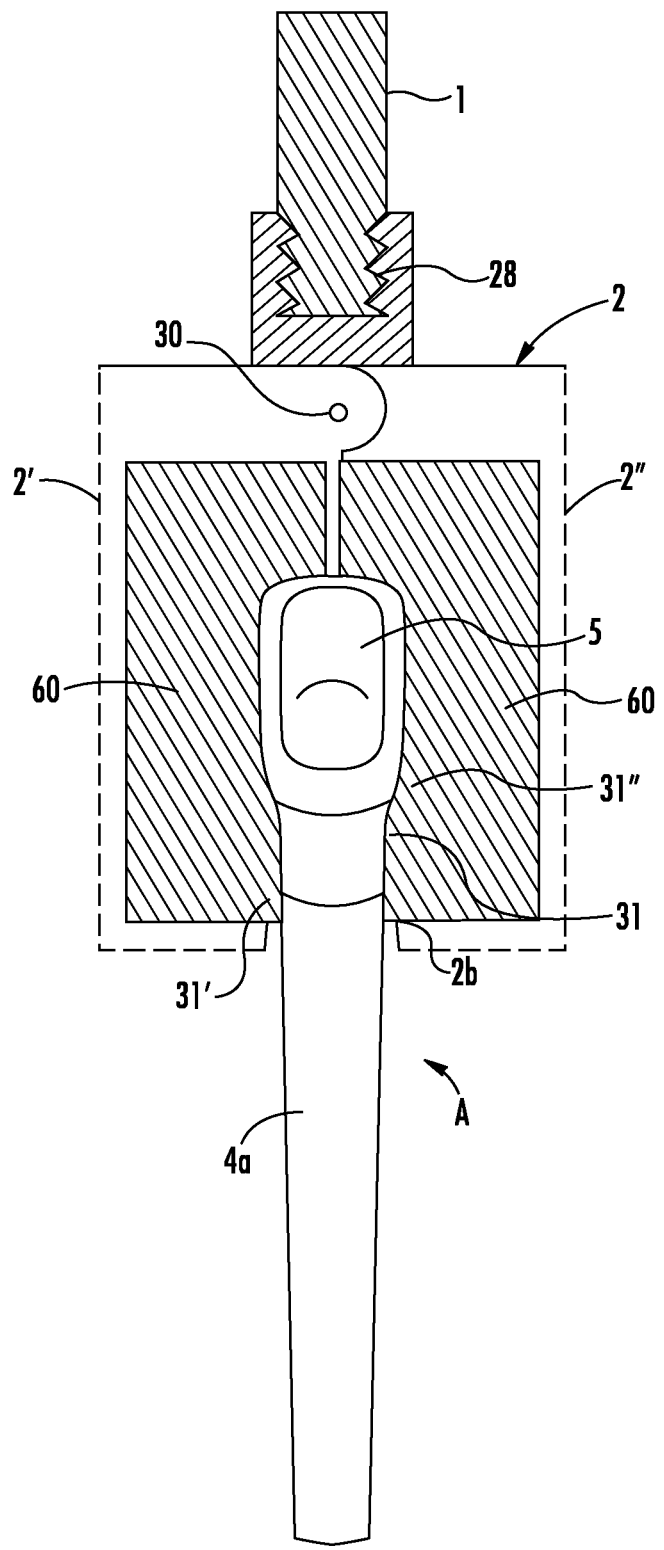
FIG. 6 illustrates a view of a further embodiment of a securement device.

With reference to the embodiment of FIG. 6, the compressible material 60 may be one which exhibits good thermal properties but very little compression. Alternatively the compressible material 60 may be substituted by a rigid, thermally insulating material which may be impact resistant to a sufficient degree that while the component part is gripped within the complementary cavity parts 31',31", impact forces exerted transmitted via the handle 1 or otherwise imparted to the impactor body 2 may be transmitted to the component part.

Figure 7:
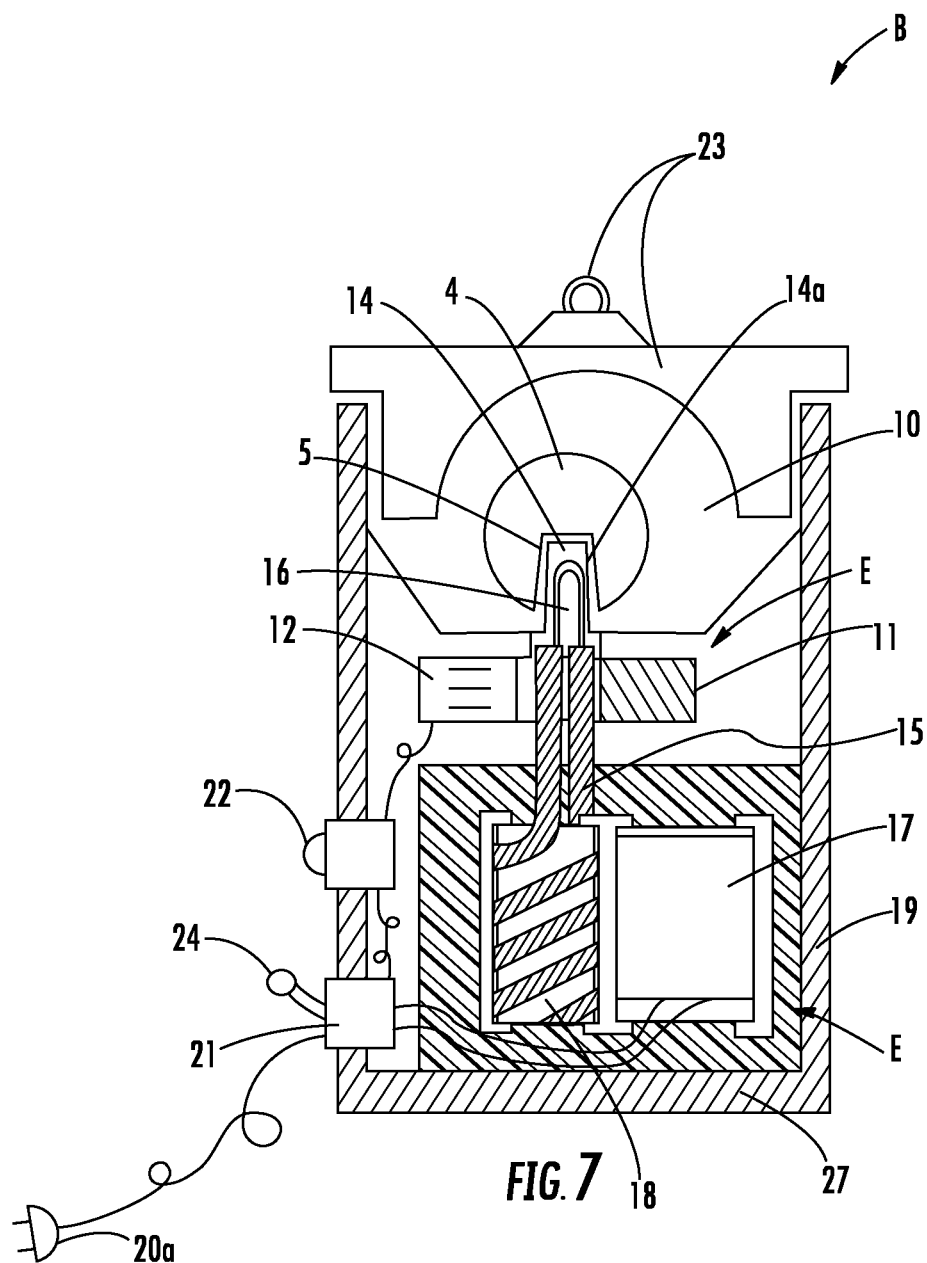
FIG. 7 is a cross-sectional view of a thermal treatment device according to a preferred embodiment, here illustrating its use in directly heating a tapered cavity present within a modular component, viz., a ball.
Figure 8:
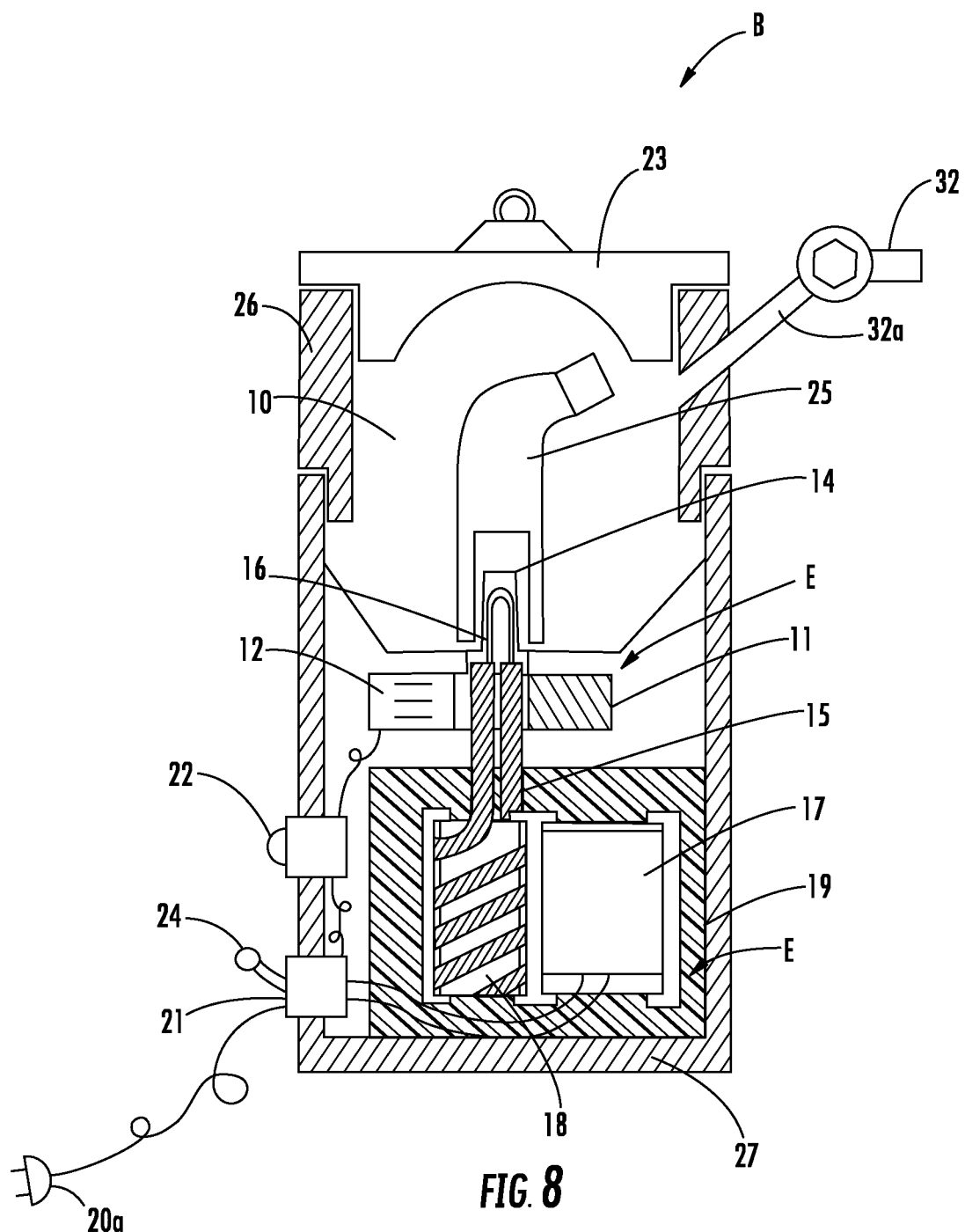
FIG. 8 is a cross-sectional view of a thermal treatment device according to a preferred embodiment, which is substantially as depicted in FIG. 3 but which further includes an extension part, and which here illustrates its use in heating a tapered cavity present within a modular component, viz., an orthopedic taper component.

In another aspect the present invention provides a thermal treatment device B embodiments of which are depicted on FIGS. 7 and 8. Thermal treatment devices impart thermal expansion to the component or part thereof. With reference to FIG. 7, thermal treatment is being provided within the cavity 5 of an articular ball implant 4. Electrical induction heating is provided by an electromagnetic unit (generally identified as "E"); such is a "dry heat" as not requiring any liquid or gaseous heat transfer media. The electromagnetic unit E is encased in enclosure 27. A primary electromagnetic coil 17 wrapped around an iron core 19 generates a strong current in a secondary coil 18, which is conveyed by low resistance and/or large electrical conduit 15 which is electrically connected with heating element 16. Said heating element 16 is situated inside heating core 14, here having a configuration of a male taper. The low resistance and/or large electrical conduit 15 passes through a thermal base 11 whcih insulates the heating core 14 and the ball 4 from the primary electromagnetic oil 17. The heating core 14 is formed of a thermally transmissive (or conducting) material which however need not necessarily itself be thermally conductive but need only be effective in transferring heat from heating element 16 to the outer surface 14a of the heating core 14. The heating core 14 is configured to be slidingly insertable within the tapered cavity 5 of the articular ball implant 4. Preferably however the dimensions of the heating core 14 is slightly undersized relative to the dimensions of the tapered cavity 5 so to avoid binding between the two components.

The depicted thermal treatment device B further comprises a variable closed circuit thermostat 12 which operates to control the temperature by controlling the duration needed to reach the required temperature and/or which may also limit the maximum operating temperature of the heating core 14. As it will be readily recognized, different heating parameters are required for different modular components having different configurations and masses, thus use of a control circuit 20 and/or variable closed circuit thermostat 12 may be used to establish a desired heating parameter suited for a particular modular component. As is also shown, but which may be optional in some embodiments there are illustrated audio visual aids such as light 22 which illuminates and which emits an audible signal (e.g., "beeps") to alert and operator that heating process has reached the desired temperature, indicating that the articular ball 4 (or other modular component) has reached the desired amount of thermal expansion and is ready to be removed from the device B. When such a condition state is reached, the control circuit 20 may also be programmed to automatically turn off electric current to the primary coil or an operator of a device may simply change the position of the switch 24 to the "off" position to turn off the electrical current to the primary coil.

In use, once the articular ball 4 is inserted onto the heating core 14, the heating chamber 10 is covered with a lid 9 so to avoid unwanted heat loss and concomitant extended time which would be needed to provide sufficient heat to the articular ball 4. Operation of the electromagnetic unit E is initiated by powering the unit via a power source, e.g., the electromagnetic unit E may be powered by electrical wall current (e.g, 110-130 v AC, or 220-230 v AC) supplied via a conventional plug 20a. Heating is initiated by moving switch 24 to an operating position, and to activate a control unit 20 which thereafter activates the primary electromagnetic coil 17. Such causes current flow through the secondary coil 18 and to the heating core 14 which reaches a suitable temperature to cause a desired amount of thermal expansion in the cavity 5 of the ball 4. Advantageously the heating core is operated to reach a temperature of between about 200° F.-500° F. (93° C.-260° C.), preferably about 250° F.-400° F. (120° C.-205° C.).

Heating of the ball 4 (or other modular component or part thereof) may be enhanced by establishing a vacuum within the thermal treatment device B; such may for example be achieved by providing a vacuum valve 32 having a tube 32a which extends into the interior of the chamber 10 of the thermal treatment device B. The vacuum valve 32 may be opened, and connected to a suitable vacuum source (not shown) thus withdrawing air from the chamber 10 outwardly via the tube 32a and the vacuum valve 32 during, but preferably prior to energizing the electromagnetic unit E. Such may be particularly useful when a modular component of a relatively larger size and/or larger mass is to be treated within the thermal treatment device B, i.e., as is depicted on FIG. 8.

Alternatively heating of the ball 4 (or other modular component or part thereof) may be enhanced by first establishing a vacuum within the thermal treatment device B and thereafter flooding the chamber 10 with an inert or a rare gas; such may for example be achieved by providing a vacuum valve 32 having a tube 32a which extends into the interior of the chamber 10 of the thermal treatment device B. The vacuum valve 32 may be opened, and connected to a suitable vacuum source (not shown) thus withdrawing air from the interior 10 outwardly via the tube 32a and the vacuum valve 32. Subsequently an inert gas or a rare gas is introduced into the chamber 10 during, but preferably prior to energizing the electromagnetic unit E. The amount of inert or rare gas may be provided such that a low pressure, equal to or less than 1 atmosphere (equal to or less than 101000 Pa) or an elevated pressure, viz. more than 1 atmosphere (more than 101000 Pa). Such may be particularly useful when a modular component of a relatively larger size and/or larger mass is to be treated within the thermal treatment device B, i.e., as is depicted on FIG. 8.

In place of an electrical induction heating apparatus which includes an electromagnetic unit (generally identified as "E" in FIGS. 7, 8) having a primary electromagnetic coil 17 wrapped around an iron core 19 which generates a strong current in a secondary coil 18, which is conveyed by low resistance and/or large electrical conduit 15 which is electrically connected with heating element 16, it is to be clearly understood that other apparatus and devices which provide a "dry heat" may be used instead in any embodiment of a thermal treatment device B of the invention, whether such is of a static configuration as shown in FIGS. 7 and 8, or of a hand-holdable configuration of a thermal treatment device later discussed with reference to FIG. 9. Such preferably are powered by an electrical current or power source and does not involve the use of any means of chemical combustion, as the latter introduces the risk of fire which is particularly hazardous. For example an electrical resistance type heater, an electrical heating coil, and/or a thermistor may be used instead. Such an electrical resistance type heater, an electrical heating coil, and/or a thermistor may be incorporated into a heating core 14 as is generally described herein. Also the control of current to such an electrical resistance type heater, an electrical heating coil, and/or a thermistor may be via a thermostat 12 which operates to interrupt electrical current flow to such an electrical resistance type heater, an electrical heating coil, and/or a thermistor when a desired temperature of the heating core 14 is reached. Advantageously the use of such a thermostat 12 to control current flow may simplify the control circuit 20, which may be reduced to a power source, an electrical resistance type heater, an electrical heating coil, and/or a thermistor wired in series with the thermostat 12 which operates to interrupt the operation of the an electrical resistance type heater, an electrical heating coil, and/or a thermistor when a desired temperature is reached.

When the ball 4 (or other modular component or part thereof) has reached a desired temperature and has undergone sufficient thermal expansion, the ball 4 may be removed from the thermal treatment device B utilizing a securement device, such a securement device A (FIGS. 1-6) which securement device may be used to join the heated ball 4 (or other modular component) to a further modular component or part thereof, which may be external of but which is preferably already implanted in a human body. To remove the ball 4, the protective lid 23 is lifted and removed to reveal the chamber 10. The securement device A is inserted such that the thermally treated ball 4 is sufficiently inserted into the cavity 31 and retained therein. Such may be by engagement of the a claw end 29 of the lever 3. The thermally treated ball 4 is promptly removed and provided to the operating surgeon at the side of the open surgical wound, and the surgeon thereafter joins the thermally treated ball 41 (or other thermally treated modular component or part thereof) with a further non-thermally treated modular component or part thereof already present within the open surgical wound. Joining may require simply inserting corresponding male and female parts of modular components together while one of the parts is in a thermally expanded condition and releasing the lever and withdrawing the securement device A, but optionally and frequently preferably before the securement device A is released from the thermally treated modular component or part thereof (here, ball 4) an impacting force, such as via a surgeon's hammer or a powered device may be used to drive the thermally treated modular component or part thereof onto or into the non-thermally treated modular component or part thereof already present within the open surgical wound so to provide a higher degree of compression of these elements, so that upon cooling of the thermally treated modular component or part thereof and thermal contraction thereof, a higher degree of compression is achieved than without the impacting force. During this placement, heat resistant skirt 6, which extends beyond the ball 4, keeps surrounding tissues from contacting the heated articular ball 4.

Optionally but preferably, after completing the junction of the thermally treated modular component or part thereof onto or into the non-thermally treated modular component or part thereof as described immediately above, the securement device A or at least the impactor body 2 which may be separated from the impactor handle 1 if so desired, is kept in place for providing ongoing thermal protection to tissues within the surgical wound in the proximity of the joined components. The "shrink fit" between the joined components is accomplished by cooling the joined components, by causing thermal contraction of the thermally treated component or part thereof and a reduction in at least one dimension. The impactor and/or impactor body 2 may thereafter be removed and if desired further cooling of the joined components and parts thereof is continued using further irrigation fluid.

Notably in view of the sufficiently high temperatures of the thermal treatment, the thermally treated component or part as well as the chamber 10 become sterilized from any living materials and pathogens such as germs and viruses.

FIG. 8 depicts an alternative embodiment of the present invention and an alternative configuration of the thermal treatment device B of FIG. 3. In FIG. 8, in place of the articular ball 4, the modular component is a revision proximal femoral implant which implant includes a tapered cavity, (a Morse taper cavity). In order to accommodate the larger size of the revision proximal femoral implant, the heating chamber 10 is enlarged by using an extension 26. Consequently, in view of the larger mass and different configuration of the revision proximal femoral implant (which is not generally spherical) it is foreseen that the thermal treatment device B will necessarily operated according to different protocols (i.e., different heat settings and/or heating times) in order to achieve the desired degree of thermal expansion of the tapered cavity of the revision proximal femoral implant.

FIG. 9 a partial cross-sectional view of both a further embodiment of a securement device A, and a hand-holdable thermal treatment device B, illustrating the direct heating of a tapered cavity 5 within a modular component, viz., an articular ball implant 4. It is to be understood however that different modular components may also be heat treated utilizing a hand-holdable thermal treatment device B as well. The a hand-holdable thermal treatment device B as illustrated in FIG. 9 offer several advantages over the heat treatment devices depicted on FIGS. 7, 8. One such advantage is the portability provided by a hand-held thermal treatment device B, as it may be brought into the near immediate proximity of an open surgical wound and it views not only to provide an initial thermal treatment to a modular component in order to provide a satisfactory degree of thermal expansion, but, should placement of the modular component require additional time or if the degree of thermal expansion is undesirably diminished prior to attachments to a further mating modular component, a hand-holdable thermal treatment device permits for re-heating of the modular component. Secondly, a hand-holdable thermal treatment device B also allows for the thermal treatment of a modular component which has a ready been inserted and is being retained within a securement device A. Such permits for an unheeded or not previously thermally treated modular component to be first placed into a securement device A and subsequently, thermal treatment in order to achieve a desired degree of thermal expansion of a modular component may take place within a part of the securement device A. Thus the step requiring the transfer of a thermally treated modular component from within a stationary thermal treatment device B (such as in FIGS. 7, 8) may be omitted. However the benefits of a stationary thermal treatment device B (such as in FIGS. 7, 8) are not to be overlooked, as in particular according to those depicted embodiments he treatment of the modular component takes place within a closed cavity, which may also be flooded with a specific gas and/or subjected to a reduced pressure. Such might provide faster thermal heating than the might be otherwise achieved by the use of a hand-holdable thermal treatment device B.

As is seen in FIG. 9, the securement device A the impactor handle 1 (partially shown) has affixed thereto by a set of mating threads 28 to an encased impactor body 2. In this embodiment the impactor body 2 is present within an external casing 70 within which is fitted the impactor body 2 and the thermal skirt 6. The impactor body 2 and the thermal skirt 6 are formed of a heat resistant material that is effective in withstanding temperatures of at least, but preferably in excess of 275° C. without deformation or melting, as has been described previously with reference to other embodiments. Preferably also, the material of construction of the casing 70 is formed of a heat resistant material is welcome; coming into consideration are metals, resins, composites, ceramics, polymers, fiberglass or combination thereof which may optionally but in some cases preferably include reinforcing material such as fibers, roving, wire, particulates. It is however noted that the thermal insulating properties of the impactor body 2 and the thermal skirt 6 not dictate that the material of construction of the casing 70 the equally, or more heat tolerant.

The securement device A in this embodiment includes one or more inner springs 8b which are positioned within that the inner cavity 31 and which are biased towards a centerline, or towards the position of the modular component when such is present within the cavity 31. Preferably two or more inner springs 8b are present, such as is illustrated in FIG. 9 shows illustrates that they are diametrically placed across from one another within the cavity 31 such that they may each comment contact with an opposed portion are surface of a modular component and, due to their spring forces, retained the modular component within the cavity 31 and the impactor body 2, Optionally but preferably, corresponding channels 6c are also present with one present beneath a corresponding inner spring 8b. These corresponding channels 6c are recessed into part of the impactor body 2 and provide a space within which a spring 8b may be retracted sufficiently so to allow for the insertion of, and also the removal of the modular component from within the cavity 31. Advantageously, as shown in the figure the profile of the inner springs 8b are such that they include a portion, preferably a contoured portion, which approximates a corresponding part of the surface of a modular component and thus comes into good interfacial contact there with as such provides improved retention of the modular component. Is of course also be understood that while to inner springs 8b are illustrated, 1, 2, 3 or any other number may be similarly provided as deemed desirable or necessary.

It is to be understood that features of securement devices A illustrated in any of the figures may be used interchangeably, as well as may be combined within a single securement device A. Thus the depicted embodiments of securement devices A are provided as illustrative but non-limiting examples.

FIG. 9 also depicts a hand-holdable thermal treatment device B, useful in providing the direct heating of a tapered cavity 5 within a modular component. Such a hand-holdable thermal treatment device B includes a barrel 14b having at an end thereof a heating core 14 which is insertable within the cavity 5 of the articular ball implant 4. The barrel 14b extends to a housing 14c having a grip 14d which is adapted to be held by a surgeon or other person. A switch 24 extends from the grip 14d; an operator of a device may simply change the position of the switch between an "on" and an "off" position to actuate the hand-holdable thermal treatment device B so to energize the heating core 14 and to provide thermal treatment to the cavity 5 of the modular component. As with the devices of FIGS. 7, 8, the heating core 14 may be indirect physical contact with a part of the modular component, viz., ball 4 or may separated therefrom by a small air gap. The hand-holdable thermal treatment device B may include one or more audio visual aids such as lights 22 which illuminate and may emit an audible signal (e.g., "beeps") to alert and operator that heating process has reached the desired temperature, indicating that the articular ball 4 (or other modular component) has reached the desired amount of thermal expansion and that the heating core 14 is ready to be removed from the cavity 5. When such a condition state is reached, as may be in response to the condition of a variable closed circuit thermostat 12 within the barrel 14b in then near proximity of the heating core 14, which thermostat 12 operates to control the temperature by controlling the duration needed to reach the required temperature and/or which may also limit the maximum operating temperature of the heating core 14. Further, a control circuit (not shown, but which may be integrated into the housing 14c and/or a power supply/control unit 20b) may also be programmed to automatically turn off power to the heating core 14, or, an operator of a device may simply release the switch 24 which moves it to an "off" position and thus terminates heating of the heating core 14.

While not shown in FIG. 9, it is nonetheless to be understood that elements of a control circuit 20 may present within the housing 14c and/or the power supply/control unit 20b to which it is electrically connected. Also while not shown in FIG. 9, it is nonetheless to be understood that all operating elements may be incorporated into the housing 14c, in which case the electrical cable is may terminate in a plug 20a which may be connected to a suitable power source.

As to a further discussion of the manner of usage and operation of the present invention, the same should be apparent from the above description. With respect to the above description then, it is to be realized that the optimum dimensional relationships for the parts of the invention, to include variation in size, material, shape, form, function and manner of operation, assembly and use, are readily apparent and obvious to one skilled in the art and all equivalent relationships to those illustrated in the drawings and described in the specification are intended to be encompassed by the present invention. Therefore, the foregoing is considered as illustrative only of the principles of the invention.

Furthermore, since numerous modifications and changes will readily occur to those skilled in the art, it is not desired to limit the invention to the exact construction and operation shown and described, and accordingly, all suitable modifications and equivalents may be resorted to, falling within the scope of the invention.

The invention claimed is:

1. A thermal treatment device which, during operation, imparts reversible thermal expansion to a part of, or to a component of a modular orthopedic prosthesis which comprises:
   an enclosure;
   an electromagnetic unit having a primary electromagnetic coil and a secondary electromagnetic coil connected to a heating element which, which when the electromagnetic unit is operating, said heating element heats a part or component of the modular orthopedic prosthesis present within the enclosure to an elevated temperature and imparts thermal expansion to the part or component.

2. The thermal treatment device of claim 1, wherein the thermal treatment device further includes a chamber containing vacuum.

3. The thermal treatment device of claim 1, wherein the device includes a pressurizable chamber containing a gas in which the gas is pressurizable to a pressure greater than i 1 atm.

4. A thermal treatment device of claim 1 which comprises:
   an enclosure which includes in its interior as a heating element: an electrical resistance type heater, and/or an electrical heating coil, and/or a thermistor which heating element is used to impart thermal expansion to a part or component of a modular orthopedic prosthesis.

5. The thermal treatment device of claim 1, wherein the electromagnetic unit is contained within the enclosure.

6. The thermal treatment device of claim 1, which further includes a lid.

7. The thermal treatment device of claim 2, which further includes a vacuum valve connected to the enclosure device and which is connectable to a vacuum source.

8. The thermal treatment device of claim 3, wherein the gas is an inert gas or a rare gas.

9. The thermal treatment device of claim 4, wherein the thermal treatment device further includes a chamber containing vacuum.

10. The thermal treatment device of claim 4, wherein the device includes a pressurizable chamber containing a gas in which the gas is pressurizable to a pressure greater than 1 atm.

11. The thermal treatment device of claim 1, which additionally includes an extension.

12. The thermal treatment device of claim 4, which additionally includes an extension.

13. A hand-holdable thermal treatment device which, during operation, imparts reversible thermal expansion to a part of, or to a component of a modular orthopedic prosthesis which comprises:
   an electromagnetic unit having a primary electromagnetic coil and a secondary electromagnetic coil connected to a heating element which, which when the electromagnetic unit is operating, said heating element heats a part or component of the modular orthopedic prosthesis present within the enclosure to an elevated temperature and imparts thermal expansion to the part or component.

14. The hand-holdable thermal treatment device of claim 13, which further comprises:
   a barrel, a grip, a switch,
   optionally one or more audio visual aids.

* * * * *